United States Patent [19]

Closmann

[11] Patent Number: 4,669,299
[45] Date of Patent: Jun. 2, 1987

[54] MEASURING RELATIVE PERMEABILITY TO STEAM IN CORES OF WATER AND OIL CONTAINING RESERVOIR FORMATIONS

[75] Inventor: Philip J. Closmann, Houston, Tex.

[73] Assignee: Shell Oil Company, Houston, Tex.

[21] Appl. No.: 837,227

[22] Filed: Mar. 7, 1986

[51] Int. Cl.⁴ ............................................. G01N 15/08
[52] U.S. Cl. ....................................... 73/38; 250/253; 73/153
[58] Field of Search ....................... 250/253, 255, 256; 73/153, 38

[56] References Cited

U.S. PATENT DOCUMENTS 3,018,660  1/1962  Schmid ............................. 73/153
4,458,520  7/1084  Adame et al. ..................... 73/38
4,486,714  12/1984 Davis, Jr. et al. ................ 73/153
4,540,882  9/1985  Vinegar et al. .................. 250/255
4,542,648  9/1985  Vinegar et al. .................. 73/153
4,608,859  9/1986  Rockley ............................ 73/153

Primary Examiner—Jerry W. Myracle
Assistant Examiner—Hezron E. Williams

[57] ABSTRACT

Relative permeabilities to flowing steam water and/or oil phases within cores of earth formations are determined by flowing such fluids at reservoir conditions, sealing them within the cores, X-ray scanning the sealed cores and determining the saturations from densities and/or tagged oil volumes and determining the permeabilities from measured pressures and temperatures.

3 Claims, 1 Drawing Figure

U.S. Patent           Jun. 2, 1987           4,669,299
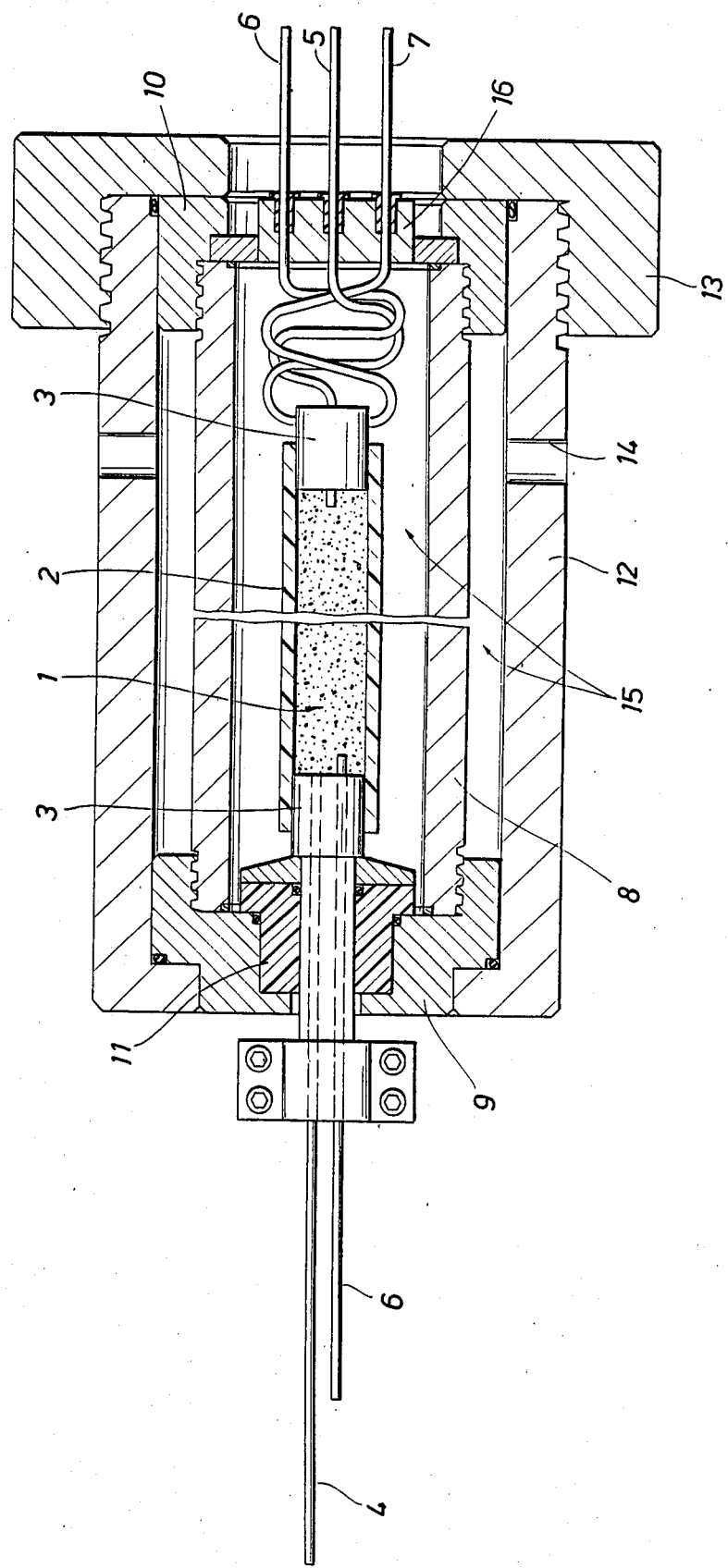

MEASURING RELATIVE PERMEABILITY TO STEAM IN CORES OF WATER AND OIL CONTAINING RESERVOIR FORMATIONS

BACKGROUND OF THE INVENTION

The present invention relates to determining properties such as relative permeability to steam or combinations of steam, water or oil phases within cores of reservoir formations containing oil and water, and is also useful for measuring permeabilities to steam, water, and oil in well defined laboratory-derived porous media such as glass bead or sand packs. In this latter application the greater stability of laboratory-derived as contrasted with some natural systems permits measurements to be made of more subtle changes in three-phase relative permeabilities.

The relative permeability to the steam phase in the presence of water and residual oil plays a significant role in simulating reservoir production performance during a steam drive. It is important to determine this parameter as accurately as possible. Previously obtained values for steam permeability have been based on gas permeabilities in gas/liquid systems and to some extent on adjusted values obtained from history matching based on oil production data. Prior measurements of such permeability have been based on geothermal systems where there is no oil phase present or in conjunction with surfactant systems. Published work relating to external gas drive with vaporization present at various temperatures suggests that the gas phase permeability is only mildly sensitive to temperature. Quantitative differences between the various published results leave some doubt as to the appropriate value to use. There is a need for measurements of the permeability to steam and simultaneously to water for cores of reservoir formations in which the residual oil is present, as well as for systems in which oil is flowing.

SUMMARY OF THE INVENTION

The present invention relates to a process for determining permeability properties of at least one fluid of the group steam, water and oil in a core sample of a synthetic or natural reservoir rock formation (hereinafter referred to as a "reservoir formation") containing at least water and oil and, possibly, gas dissolved in or in addition to the oil. A core of a reservoir formation containing at least oil and water is mounted within a flexible-walled impermeable tube means arranged for fluid to be flowed through the core. The core-containing flexible walled tube means is mounted within a relatively rigid-walled container having fluid impermeable walls which are permeable to X-rays and pressurized to at least substantially the pressure existing in the reservoir. The heat loss properties of the relatively rigid walled chamber are arranged so that the rate of heat loss from the core is sufficient to condense some, but not all, steam which is flowed through the core while limiting the heat loss from the injection point to an extent allowing the input temperature to be controlled. For measurements at residual oil steam of selected quality is flowed through the core at a selected rate and temperature until an equilibrium is attained at which substantially no more oil is produced. For three-phase measurements steam, water, and oil are flowed through the core until a steady state or equilibrium pressure drop is attained. The rigid-walled chamber is then sealed while it contains the fluids present at said equilibrium and the core within it is subjected to an X-ray scan. The permeability properties are then determined on the basis of the extent of depletion of the original oil saturation and the respective inflow and outflow pressures, indicative of the pressure drop across the core, and temperatures corresponding to the equilibrated flow of steam through the core.

BRIEF DESCRIPTION OF THE DRAWING

The drawing is a schematic, longitudinal, cross-sectional illustration of a vessel assembly suitable for use in the present invention.

DESCRIPTION OF THE INVENTION

In effect, the present invention provides a means of obtaining an average value for at least one permeability property of a core sample of a reservoir rock formation. The invention utilizes a steady state situation attained in a manner such that the permeability and saturation are essentially constant along the core.

For measurements indicative of properties within a subterranean reservoir formation, it is important that the core contain the fluids which were in place within the reservoir formation at the time of the coring. Compressive stresses on the core substantially equalling those of the overburden are preferably maintained on the core during the entire testing operation. The temperatures and pressures at which steam is flowed through the core should be arranged to avoid any depletion of the water phase by evaporation.

The pressurized core containing the fluids present during the equilibrated flow of steam should be scanned by a computerized axial tomographic (CAT) scanner to determine the attenuation coefficients at a plurality of points in the cross section of the core sample. CAT scanning devices and techniques are currently known and available. Particularly suitable techniques include scanning the cores at two different energy levels as described in U.S. Pat. No. 4,540,882. One such scan is preferably performed at an energy low enough to predominate in the photoelectric region, i.e., less than about 80 Kev mean energy, with another scan being performed at an energy high enough to be predominantly in the Compton region, i.e., greater than about 80 Kev mean energy. Either preimaging or post-imaging techniques can be applied to the attentuation coefficients obtained by the dual energy scans for determining the effective atomic number of the core sample. The saturation of fluid within the core can then be determined by an operator who reviews the atomic number image to determine the saturation in each cross section analyzed. Alternatively, the CAT system controller and data processing equipment can be arranged to implement a method which automatically determines the portion of the core which is permeated by fluid. For example, the effective atomic number can be determined for reference area in the center of the core sample and for a plurality of areas that are positioned at different distances from the center of the core sample. The average effective atomic number for the reference area can then be compared with the average effective atomic number for a plurality of areas to determine which of the plurality of the areas has an average effective number that is greater than the average effective atomic number of the reference area by a predetermined amount, as an indication of the fluid saturation of the core.

The drawing shows an apparatus system suitable for use in the present invention. The apparatus can suitably be composed of components which are individually known and are available. A reservoir core 1 is mounted within a flexible, fluid impermeable, tubular sheath 2. The tubular sheath is preferably closed by a pair of piston 3 so that fluid pressure can be applied to all sides of the core, in order to simulate the overburden pressures within the reservoir formation.

Fluid inlet and outlet tubes 4 and 5 are arranged for flowing fluid through the core. Conduits such as 6 and 7 for thermocouple and pressure measuring means are provided for measuring the pressures and temperatures of fluids within the core.

The flexible walled core-containing arrangement is disposed within a relatively rigid walled container having a body 8 composed of fluid impermeable, X-ray permeable material such as aluminum, and end closure assemblies 9 and 10.

An important feature of the present invention is arranging to have a small controlled heat loss within the core in conjunction with operating pressures and temperatures in the core and at the inlet and outlet ends so that no net evaporation of water occurs within the core while maintaining sufficient heat loss to form some condensate within the core. Applicants have found that this can be attained by surrounding a relatively small steam input tube, such as a ⅛th-inch stainless steel pressure tube welded into appropriate ports, then insulating the input tube with a relatively thick cylinder of heat resistant, thermal insulating material. A particularly suitable insulating material is Vespel resin, manufactured by DuPont Company. Without the relatively extensive heat insulation, the heat loss to such a rigid walled container tends to be so extensive that the desired steam temperature can be maintained in only the immediately adjacent end of the core. In a preferred embodiment, a hollow chamber is drilled in an inlet piston so that a heat generating cartridge can be inserted to supply additional control of the heat. In addition, in situations in which relatively high pressures and temperatures are to be employed, a rigid walled container such as aluminum is preferably enclosed within a pressure equalizing jacket, such as jacket 12, with a removable closure ring 13, and at least one inlet port 14 for a pressurizing fluid. In one application of this apparatus, a heating tape (not shown) is wrapped around the outside jacket 12 so as to maintain the outer temperature some small increment below the outlet steam temperature. In this manner, the heat loss from the core can be limited and controlled, and the outlet steam quality can be controlled.

As indicated in the drawing, the junctions between components of the rigid walled vessel 8 and pressure equalizing jacket 12, as well as between the rigid walled vessel and the pressure equalizing jacket, are preferably sealed with appropriate seal rings such as the commercially available Kalraz O-rings to ensure that the containers are fluid-tight.

The annular spaces 15 between the flexible sheath containing core 2 and the surrounding rigid walled vessel body 8 and between the body 8 and the pressure equalizing jacket body 12, are filled with a heat resistant, relatively incompressible pressurizing liquid. A slurry of solid particles such as vermiculite in a silicone oil is particularly suitable for such a liquid. The suspended particles tend to reduce convective current-induced heat losses.

Where the rigid walled vessel 8 is composed of material as structurally weak as aluminum and the desired pressures and temperatures are relatively high, such as those in the order of 400° to 500° F. at pressures of about 1500 psi, it is desirable to remove the net load on such a material by surrounding that vessel with a steel jacket and pressurizing both of the annular spaces 15 to the operating pressure. (The inlet into the annulus between vessel 8 and jacket 12 consists of an entrance port in end piece 16 in the plane containing the production tap perpendicular to the plane of the drawing.)

The pressurized core-containing assembly is preferably warmed to the desired temperature by initially flowing through the core increasingly hot portions of an aqueous saline solution which is, or is substantially equivalent to, the fluid in the reservoir being sampled. Subsequently, the steam of the quality, temperature and pressure to be measured is circulated through the core until the equilibrium is attained. After equilibrium is reached under the selected flow conditions, the fluid lines to and from the core are sealed and the assembly is allowed to cool down to room temperature with the overburden pressure being maintained on the fluid-containing core. When that assembly is cool, the pressurizing jacket, if used, is removed and the rigid walled container, still containing the core under overburden pressure, is subjected to CAT scanning measurements for liquid saturation. In such measurements, the X-ray adsorption at each location provides a bulk density at that place. From the bulk densities in conjunction with a knowledge of the oil saturation, calculations can be made of the water saturation. The oil saturation can be measured by measuring the amount of oil displaced from the core and/or by loading the oil phase with iodooctadecane or other radioactively (or nonradioactively) tagged oil soluble material and scanning the core at appropriate X-ray energies, or the like.

In general, the present process can be applied to substantially any water and oil containing reservoir formation for determining the relative permeability of that formation to a steam phase in the presence of water and residual oil or permeability to steam, water and oil phases as a function of liquid oil and water saturations.

What is claimed is:

1. A process for determining permeability properties of at least one fluid of the group consisting of steam, water and oil in a sample of reservoir rock formation containing fluid phases inclusive of at least oil and water phases, comprising:

providing a core of the reservoir formation containing oil and water;

mounting the core within a flexible walled, impermeable, tubular sheath means arranged for flowing fluid through the core;

mounting the flexible walled core-containing means within a relatively rigid walled container having fluid impermeable walls which are permeable to X-rays and pressurizing the core within the rigid walled container to a pressure approximating that of the reservoir formation;

arranging the heat loss properties of the rigid walled chamber so that the rate of heat loss from the core is sufficient to condense some, but not all, steam flowing through the core while limiting the heat loss near the steam inlet into the chamber so that the temperature and steam quality can be controlled at the inlet and at least substantially throughout the core;

flowing at least one fluid of the group consisting of steam, water and oil through the core at a selected rate and temperature until an equilibrium is attained at which the rate at which oil is produced becomes substantially constant;

sealing the rigid walled container while it contains the fluid and fluid pressure that was present when said equilibrium was attained;

X-ray scanning the sealed chamber to determine the bulk density all along the core; and determining said permeability properties from the properties of the fluids flowed into and out of the core and the pressure drop across the core.

2. The process of claim 1 in which the core to be pressurized, is surrounded by both a rigid walled container and a pressure equalizing jacket, and is pressurized by at least substantially equally increasing the pressure within the pressure equalizing jacket and the pressure inside the core-containing, rigid walled container.

3. The process of claim 2 in which the heat loss properties of the core pressurizing chamber within the pressure equalizing jacket are controlled by surrounding the steam inlet with a significantly thick layer of heat resistant, thermal insulating material.

* * * * *